United States Patent [19]
Tyler

[11] Patent Number: 5,123,477
[45] Date of Patent: Jun. 23, 1992

[54] THERMAL REACTOR FOR BIOTECHNOLOGICAL PROCESSES

[75] Inventor: Jonathan M. Tyler, Edmonton, Canada

[73] Assignee: Unisys Corporation, Blue Bell, Pa.

[21] Appl. No.: 346,412

[22] Filed: May 2, 1989

[51] Int. Cl.$^5$ ............................................. F25B 29/00
[52] U.S. Cl. .................................... 165/2; 165/12;
 165/30; 165/48.1; 236/15 BB; 236/78 B;
 236/91 A; 236/91 D; 236/91 F; 935/85;
 935/88; 422/116; 364/557; 435/290
[58] Field of Search .............. 165/2, 30, 12, 53, 61,
 165/48.1; 236/78 B, 15 BB, 46 R, 91 A, 91 D,
 91 F, 44 C, 46 F; 62/408, 418; 435/289, 290;
 935/85, 86, 87, 88; 422/116; 364/557

[56] References Cited

U.S. PATENT DOCUMENTS

| | | | |
|---|---|---|---|
| H193 | 1/1987 | Bitner et al. | 236/15 BB |
| 1,859,613 | 5/1932 | Bailey | 165/11.1 |
| 2,801,799 | 8/1957 | McColloch | 236/46 F |
| 3,097,836 | 7/1963 | Beggs et al. | 236/15 BB |
| 3,252,258 | 5/1966 | Blizkmann et al. | 165/53 |
| 3,765,237 | 10/1973 | Blackner et al. | 219/400 |
| 4,003,728 | 1/1977 | Rath | 165/3 |
| 4,117,881 | 10/1978 | Williams et al. | 236/78 B |
| 4,327,799 | 5/1982 | Scheiwe et al. | 236/78 B |
| 4,336,329 | 6/1982 | Hesse | 435/290 |
| 4,429,829 | 2/1984 | Dutton | 236/78 B |
| 4,734,872 | 3/1988 | Eager et al. | 364/557 |
| 4,865,986 | 9/1989 | Coy et al. | 435/290 |

FOREIGN PATENT DOCUMENTS 2056694  5/1980  United Kingdom ............... 165/61

OTHER PUBLICATIONS

Advertisement in AG Biotechnology News, dated Jan–Feb, 1989 p. 26 by Eppendorf.
Advertisement in Laboratory Product News, Jan. 1989 p. 9 by Eppendorf.
Advertisement in Cell, vol. 56, No. 1, Jan. 13, 1989 by Promega Corporation, Ericomp and M. J. Research Inc.

*Primary Examiner*—John K. Ford

[57] ABSTRACT

A thermal reactor, and a method of operating the thermal reactor, in which the thermal reactor includes: a chamber which is thermally isolated by refrigerated air circulating in the walls of the chamber, and which holds a tray of sample vials; means for supplying air to the chamber and for exhausting air from the chamber; heaters for heating the air supplied to the chamber; sensors for sensing the temperature of the air supplied to the chamber and of the sample vials, and a computer which pulses the heaters according to the measured temperatures of the vials and the air in the chamber to maintain the temperature of the vials at a desired level.

18 Claims, 7 Drawing Sheets

THERMAL REACTOR FOR BIOTECHNOLOGICAL PROCESSES

FIELD OF INVENTION

This invention relates to devices which provide controlled environments for carrying out biotechnological processes, and to a method of controlling the temperature of a biotechnological process.

BACKGROUND OF THE INVENTION

Numerous biotechnological processes require temperature cycling within a defined range. These include peptide sequencing, DNA construction, DNA amplification, denaturation kinetics and probe research.

Various instruments have been constructed to provide temperature cycling. These are typically water or oil baths such as the one provided by Perkin-Elmer which includes a recirculating oil bath with chillers and heaters in an aluminum block. It is programmable and will run a preselected temperature profile. It controls the temperature of up to 48 test tubes and utilizes one or two temperature sensors to sense the proper temperatures.

In this and other prior devices, precise temperature regulation has been found difficult to attain. Systems which rely upon circulating liquids for temperature control tend to have many moving parts which can fail, and the recirculating liquids cannot accurately control temperature. Temperature ramping in such liquid systems tends to be non-uniform over time because of a gradual drift of the controlling liquids towards equilibrium. In the Perkin-Elmer apparatus, oil may contaminate the outside of the sample tubes. Further disadvantages may include the necessity to adjust the cycling to accommodate changing environmental conditions, and multiple diagnostic tests to assess the instrument's performance. Water bath systems also have a slow response time, and require expensive, large capacity water baths.

SUMMARY OF THE INVENTION

The present invention provides a novel design of programmable temperature control device which utilizes air flow, and overcomes many of the disadvantages of the prior devices. In one embodiment of the invention, there is provided a thermal reactor for cyclic heating and cooling of samples, the thermal reactor comprising:

a chamber having means for securing the samples within the chamber;

air passage means connected to the chamber for supplying air to the chamber and exhausting air from the chamber;

heating means disposed within the air passage means;

first temperature sensor means disposed within the chamber for sensing the temperature of a representative one of the samples, the first temperature sensor means having a first output representative of the temperature of the sample;

second temperature sensor means disposed within the chamber or air passage means for sensing the temperature of the air supplied to the chamber, the second temperature sensor means having a second output representative of the temperature of the air within the chamber; and control means connected to the first temperature sensor means, the second temperature sensor means and the heating means for controlling the temperature of the air supplied to the chamber in response to receiving the first and second outputs.

BRIEF DESCRIPTION OF THE DRAWINGS

There will now be described a preferred embodiment of the invention, with reference to the drawings, by way of illustration, in which.

DESCRIPTION OF THE PREFERRED EMBODIMENT

Overview

The primary components of the invention are:

(a) a chamber which is preferably thermally insulated by refrigerated air circulating in or around the walls of the chamber, and which holds a tray of sample vials;

(b) air passage means, for example, air hoses or pipes or the equivalent and turbines or fans circulating air in the hoses or pipes, the air passage means being connected to the chamber for supplying air to the chamber and for exhausting air from the chamber;

(c) heating means, for example, electrical resistance heaters or the like, disposed so that air entering the chamber passes close to the heating means;

(d) a temperature sensor that senses the temperature of the inside of a representative one of the sample vials;

(e) a temperature sensor that senses the temperature of the air within the chamber; and (f) control means, for example a computer, which regulates the temperature of the air entering the chamber based on the feedback from the two temperature sensor means.

Physical Configuration

Figure 1:
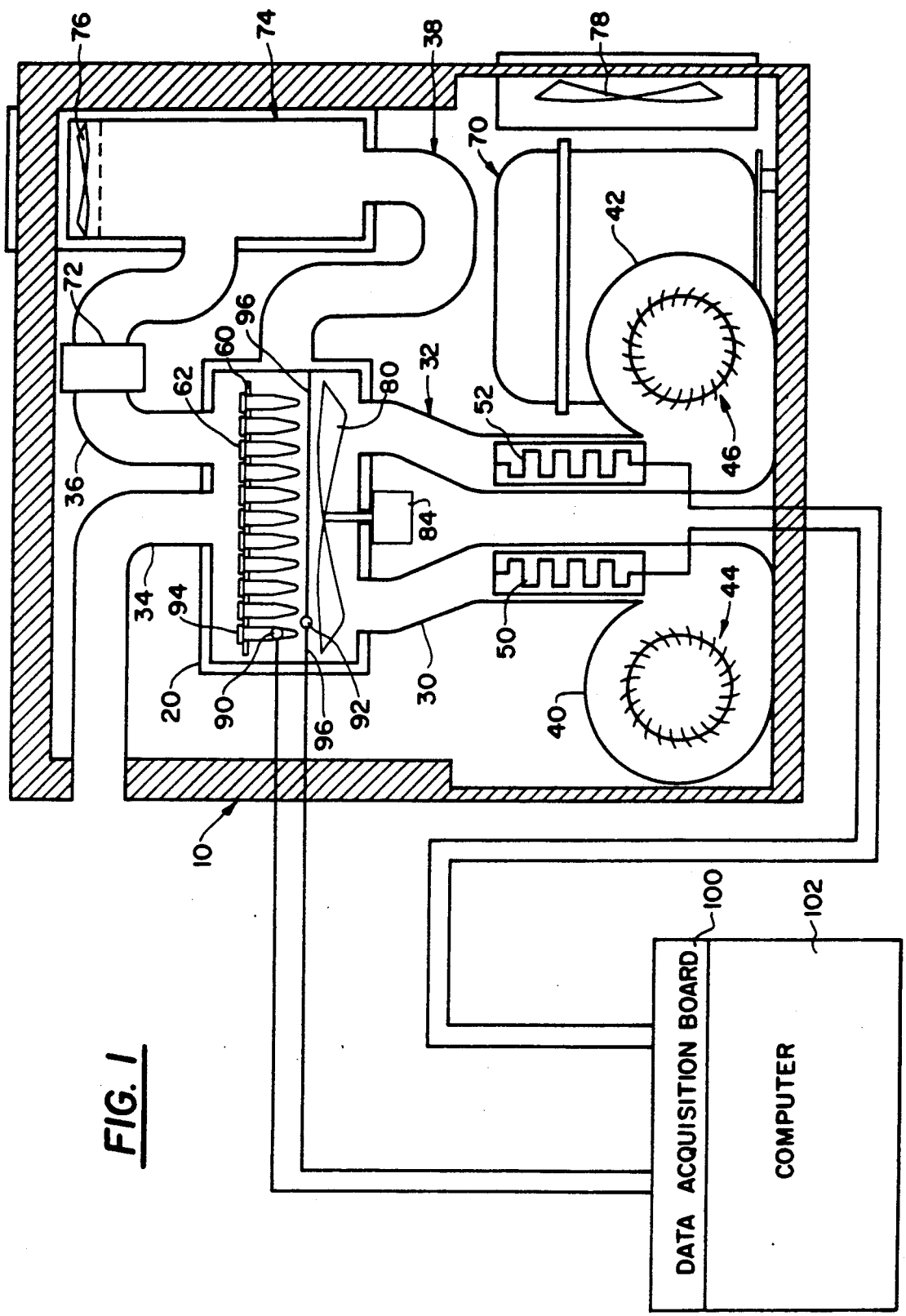
FIG. 1 is a schematic of a thermal reactor according to t he invention.

Referring to FIG. 1, housing 10 holds the component parts of the thermal reactor except for the data processing equipment. Housing 10 may be for example a Danby Model D55X 40 watt refrigerator cabinet, approximately 19"×17.5"×16.5". The door of the refrigerator cabinet is replaced by an acrylic panel (not shown) with an access opening for the chamber 20. Chamber 20 is mounted within a central portion of the housing 10, allowing room for the peripheral equipment, and defines the controlled environment for carrying out biotechnological processes.

Flexible air hoses 30, 32, 34, 36 and 38 are each connected to the chamber 20. Each of the air hoses 30, 32, 34 and 36 communicates with the interior of the chamber 20, and air hose 38 communicates only with the wall of the chamber as described below.

Primary turbines 40 and 42 are mounted within the housing 10 and are connected to air hoses 30 and 32 respectively. The primary turbines 40 and 42 draw air from the outside of the housing 10 through openings 44 and 46 of the housing 10. The primary turbines 40 and 42 may be for example squirrel cage fans rated at 120 cubic feet per minute, and are operated under instruction from the computer 102 as described below.

Heaters 50 and 52 are secured within the air hoses 30 and 32 respectively, and may be for example, 475 watt resistance heaters.

Sample tray 60 is slidably secured within the chamber 20 and includes openings for receiving vials 62. The sample tray 60 is made of polycarbonate to withstand the high temperatures to which the chamber 20 is subject.

Air hose 34 is centrally located at the top of the chamber 20 and connects directly to the outside of the housing 10 to provide an exhaust outlet. Air hose 36 is connected to the top of the chamber 20 at a position offset from the air hose 34 and connects through solenoid valve 72 to freezer chamber 74. Solenoid valve 72 opens and closes the air hose 36 under instructions from the computer 102 as described below.

Freezer chamber 74 is cooled by refrigeration unit 70, and air from the freezer chamber 74 is driven by fan 76 into the air hoses 36 and 38. The compressor of refrigeration unit 70 is cooled by fan 78. Fan 78 is mounted adjacent to an opening (not shown) in the housing 10, and may be for example a 100 cubic feet per minute cooling fan, 4.75"×4.75".

A fan 80 is driven by a 2400 rpm, 12 volt, 100 milliamp motor 84 which is connected to the lower wall of chamber 20. The fan 80 circulates the air within the chamber at about 1000 rpm. The blades of fan 80 pass over the outlets of air hoses 30 and 32, interrupting the laminar flow of air from the air hoses 30 and 32, and create a turbulent inwardly spiralling, rapidly moving flow of air within the chamber 20.

Temperature sensors 90 and 92, for example, each Model No. AD 590JH, sense the temperature in a sample vial 94 and the temperature of the air within the chamber 20, respectively. The temperature sensor 90 may be immersed in oil, air or mercury, and should be chosen so as to be representative of the temperature in all of the vials. The temperature sensor 92 is suspended by wires 96 within the chamber 20, and should be placed in a location which is representative of the temperature of the air within the chamber 20.

The temperature sensors 90 and 92 and the heaters 50 and 52 are connected to data acquisition board 100, for example a DA/M 100 available from Data Acquisition Management Corp. The data acquisition board 100 is connected to computer 102, which may be for example a Toshiba 8086 based lap top with LCD display, 640 kbytes RAM, and a 3½—720 kbytes disc drive. Computer 102 controls the operation of the thermal reactor as described below.

Construction of the Sample Chamber

Figure 2:
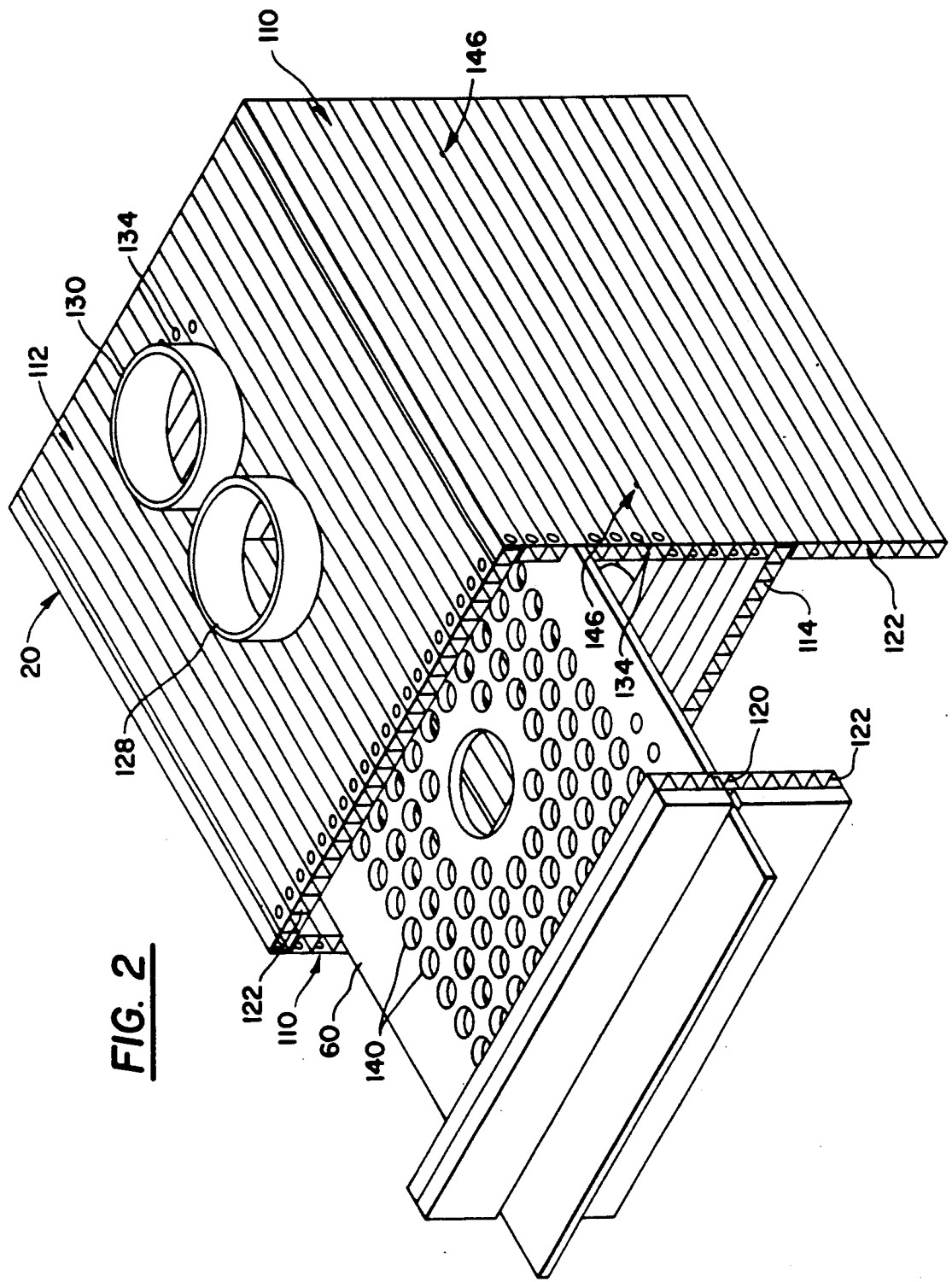
FIG. 2 is a perspective of a sample chamber for a thermal reactor according to the invention.
Figure 3:
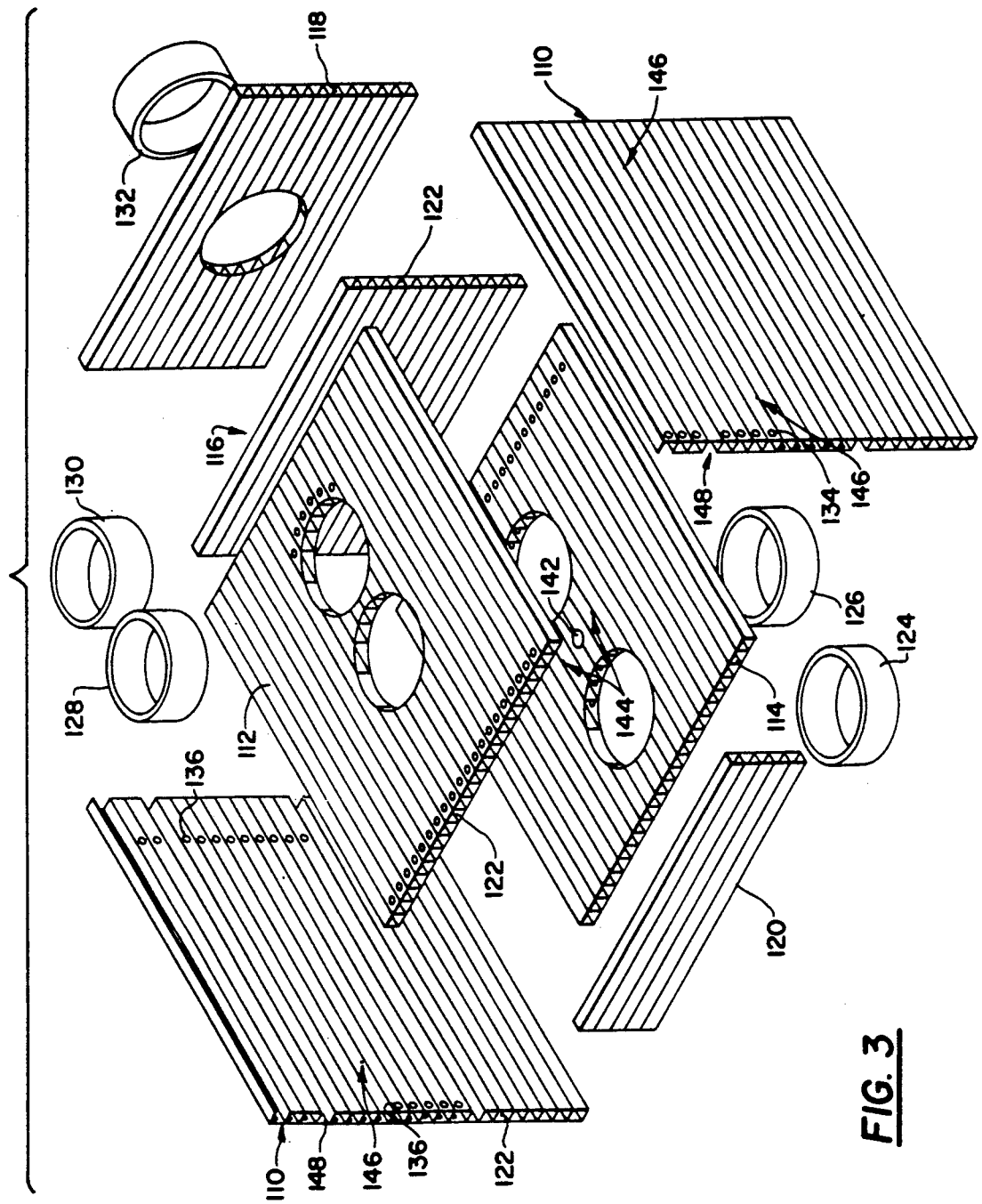
FIG. 3 is an exploded view of the sample chamber of FIG. 2.

Referring to FIGS. 2 and 3, chamber 20 is made of double layered polycarbonate. Each of the polycarbonate layers is 0.030"thick. A convenient size of chamber 20 is 14 cm.×14 cm.×7 cm. Side walls 110, upper wall 112, lower wall 114, inner back wall 116, outer back wall 118, and front wall 120 are each glued together and veined by channels 122 which allow refrigerated air to enter from air hose 38 and circulate around the walls of the chamber. Air hose connectors 124 and 126 for the supplying of air to the chamber, air hose connector 128 for the exhausting of air from the chamber and air hose connector 130 for the supplying of refrigerated air to the chamber are provided for connection to the air hoses 30, 32, 34 and 36 respectively. The channels 122 in the walls of the chamber 20 also provide added strength to the walls. Slot 148 is provided to receive the tray 60.

Outlet holes 134 are provided to allow exhaustion of the refrigerated air pumped around the walls of the chamber 20. Holes 136 connect the veins of adjacent walls and allow refrigerated air to circulate from wall to wall. Refrigeration of the chamber walls allows carefully controlled temperature changes within the chamber 20.

Tray 60 includes holes 140 for holding the sample vials 62. The vials 62 are made of polyethylene and are relatively heavy walled, and thus provide a filter function for heat transfer to and from the vials 62. Additional holes 142 and 144 are provided for the shaft of the fan 80 and for securing the motor 84. Holes 146 are provided for the wires 96.

Air is forced into the chamber 20 through air hoses 30 and 32 and spirals into the centre of the chamber and out the central air hose 34.

The location of the vials 62 is determined experimentally using several sensors subject to the constraints: (1) that they reach a temperature plateau at the same time; and (2) they ramp at the same rate.

The locations of the temperature sensors 90 and 92 are determined by trial and error to be representative of the temperature of the inside of the vials 62 and the air in the chamber 20, respectively.

Turbulence Creating Fan

Figure 4:
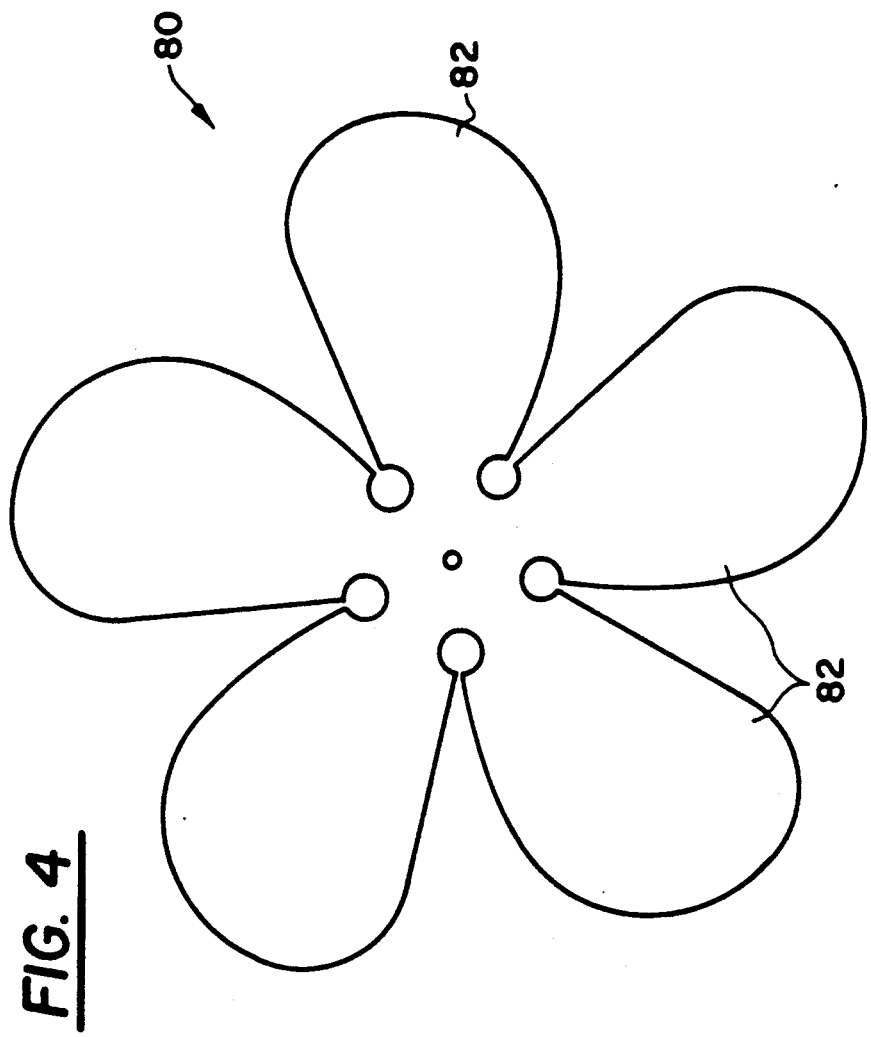
FIG. 4 is a plan view of a fan which is located in the chamber of FIG. 2.

Referring to FIGS. 1 and 4, fan 80 is located within the chamber 20 and acts to distribute the heated and cooled air rapidly around the chamber so that the chamber air temperature may be uniformly increased or decreased. Fan 80 has five blades 82, made of thin aluminum, and each having a pitch of about 20°.

Electrical Circuitry

Figure 5:
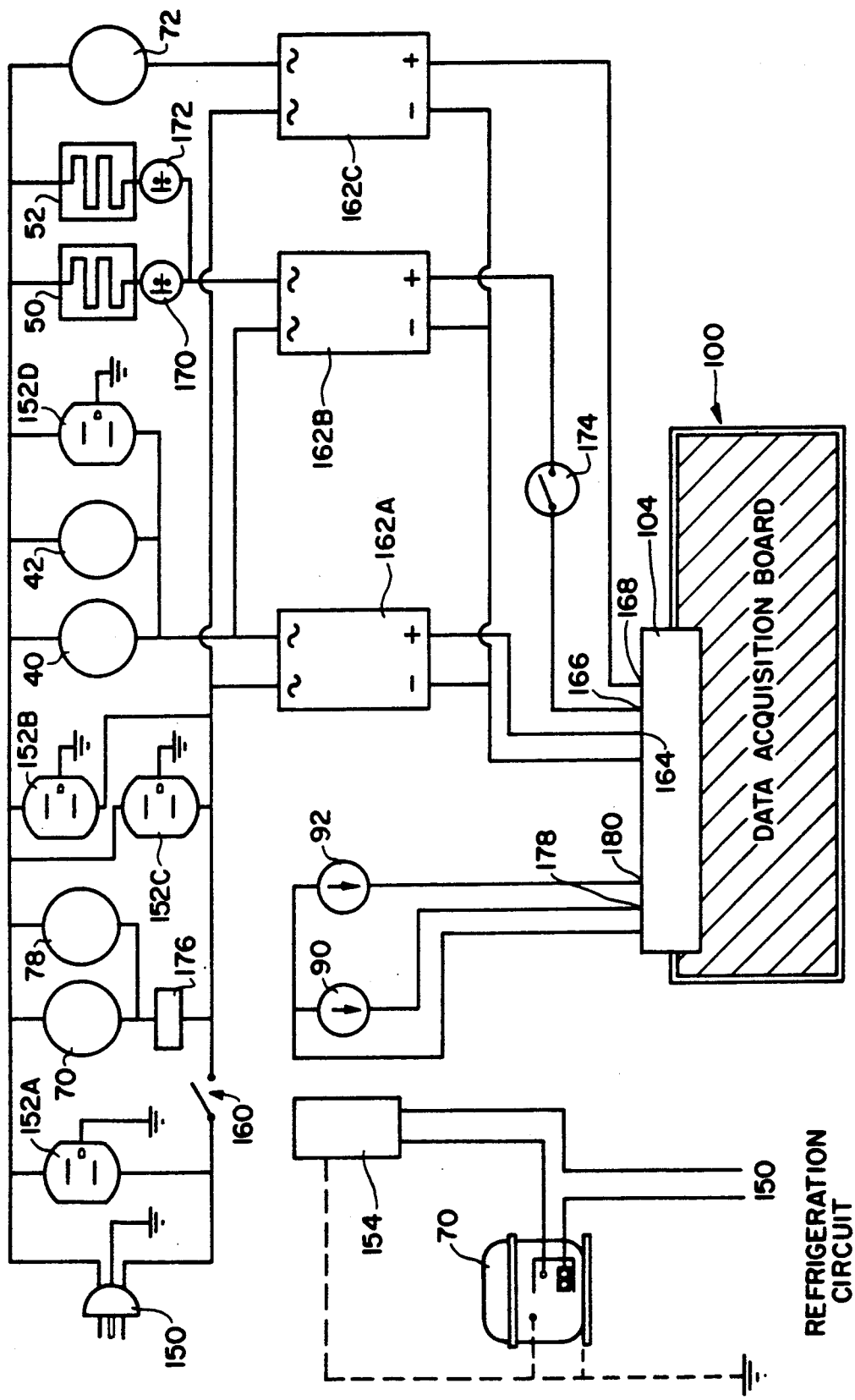
FIG. 5 is an electrical schematic of a thermal reactor according to the invention.

FIG. 5 shows a schematic of the primary electrical circuits of the thermal reactor. Plug 150 supplies power to:
(1) the computer 102 through outlet 152A,
(2) a 12 volt transformer (not shown) through outlets 152B and 152C (outlet 152 D is a spare),
(3) the refrigerator 70 and compressor fan 78,
(4) primary turbines 40 and 42,
(5) heaters 50 and 52 and
(6) cooling solenoid 72.
The main on/off switch is shown at 160.

Turbines 40 and 42, heating elements 50 and 52 and solenoid 72 are controlled through triacs 162A, 162B and 162C respectively by connection to data acquisition board 100 through digital outlets 164, 166 and 168 in header 104. Triacs 162A, 162B and 162C may be for example model no. RS104 rated at 240 VAC, 10 amp and 3-32 VDC.

The thermal relays 170, 172 and 174 shut down the heaters 50 and 52 in case of local overheating in the air hoses near the heaters 50 and 52 or in the exhaust air hose 34. Thermal relays 170 and 172 are located near the heaters 50 and 52 and are set at 150° C. Thermal relay 174 is located in the exhaust air hose and may be for example model no. ECG8118RP set to cut out at 128° C.

Thermal relay 176 is built into the refrigeration unit 70. Sensors 90 and 92 are connected to the data acquisition board 100 at 178 and 180 through amplifiers (not shown). The triac 162B is wired to the triac 162A so that the heating elements 50 and 52 are not on unless the turbines 40 and 42 are on.

The computer 102 includes a memory to load a temperature profile that is to be run and software to run the system as described below. Fail safes are provided within the software to prevent excessive run temperatures (greater than 150°) or excessive ramp rates (greater than 5° C. per second). If all fail safes fail, the computer is set to shut off all of the electrical elements in the thermal reactor except for the turbines and fans inside the reactor. The compressor of refrigerator unit 70 is also shown in FIG. 5 and is connected to its thermostat 154, located in the freezer chamber 74.

Operation of the Thermal Reactor

The thermal reactor cycles the temperature of the sample vials 62 in the chamber 20 at between 15° and 100° C. at rates of up to 5° C. per second.

Figure 6:
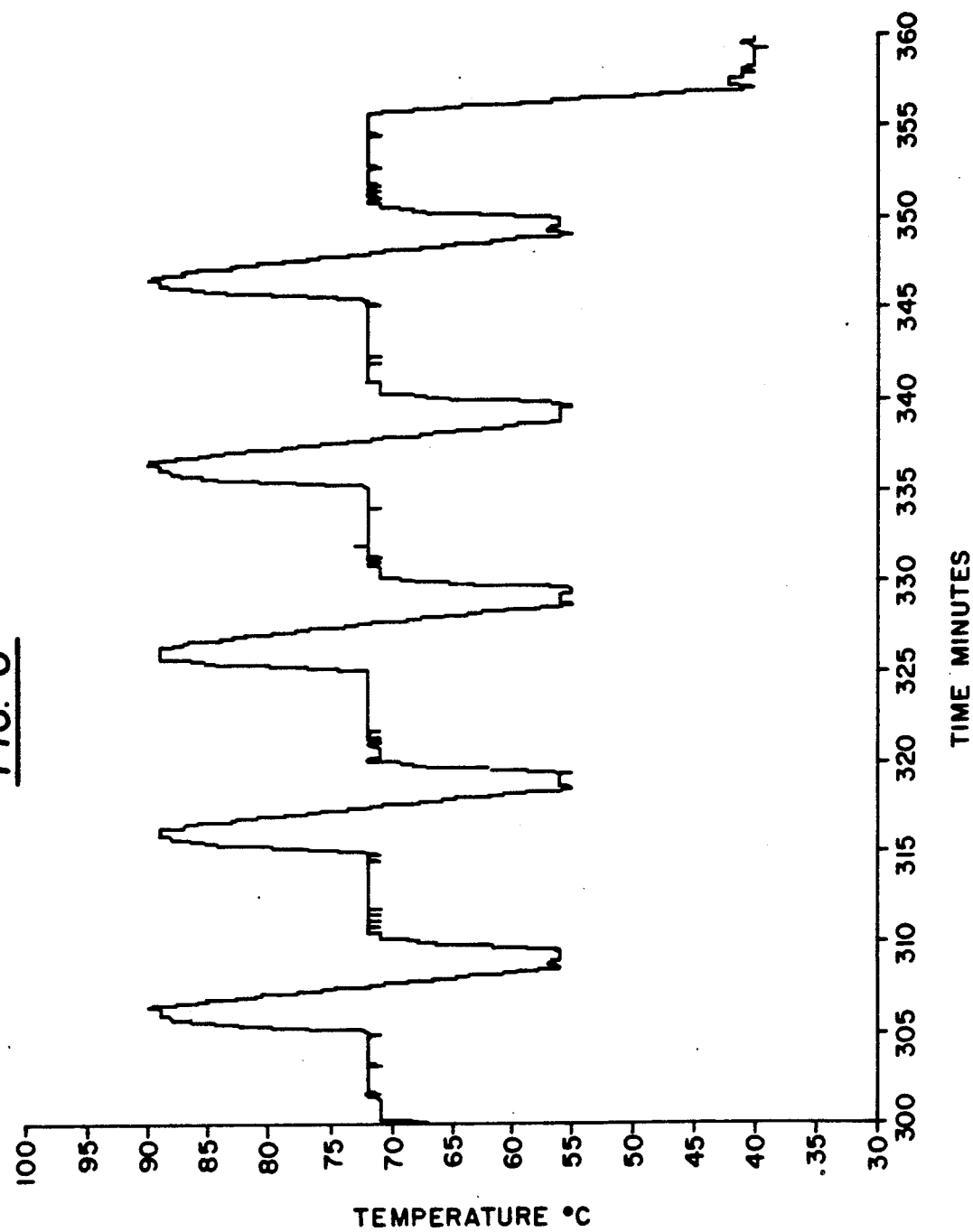
FIG. 6 is a graph showing a desired profile of temperature changes which may be run by a thermal reactor according to the invention.

To begin operation, samples are loaded into the vials 62 in the chamber 20. The sensors 90 and 92 are calibrated by known techniques. Next, the desired temperature profile to be run is loaded into the computer. An example of such a temperature profile is shown in FIG. 6.

Next, the thermal reactor is run using software designed for the purpose. The turbines 40 and 42 are turned on to deliver air to the chamber 20. Throughout the run, the turbines 40 and 42 are maintained on. During the heating cycle (ramping), the heaters 50 and 52 are turned on full for maximum ramping, and hot air is delivered to the chamber.

The temperature sensors 90 and 92 are monitored ten times per second throughout the run. When the temperature in the sample vial is within 3.5° C. of the maximum temperature desired (for example at 180 in FIG. 7), the heaters 50 and 52 are turned off. Since the turbines 40 and 42 are still running, cool air from the outside floods the chamber through hoses 30 and 32. Before the sample vial temperature, as indicated by the temperature sensor at 90, comes down to the desired level at which the temperature is to be maintained, the heaters 50 and 52 are turned on and are pulsed as required, up to ten times per second, to heat the air in the chamber 20 through a range of 6° to 7° centigrade, and thus to maintain the temperature level within the sample vial constant.

The actual ramping and maintenance functions are determined by various factors, such as the thickness of the sample vials 62.

During maintenance of the temperature in the sample vial at a fixed temperature, the computer 102 continuously samples the vial temperature at ten times per second. If the temperature in the sample vial drifts, for example downward, the computer 102 looks to see if the air temperature as indicated by the sensor 92 is above or below the desired temperature of the sample vial. If the temperature of the air is above that of the vial temperature, then the heaters 50 and 52 will not be pulsed in that one-tenth of a second, since, due to the temperature differential between the sample vial and the air, the temperature of the sample vial will begin drifting upward towards the desired temperature.

If the temperature of the air is below that of the vial temperature then the heaters 50 and 52 will be pulsed in that one-tenth of a second, and this process will continue until the air temperature is greater than the vial temperature.

Cooling of the sample vial temperature is achieved by turning off the heaters 50 and 52 and allowing cool air from outside the chamber 20 to flood the chamber 20. For heating during the maintenance cycle, as at the beginning of the cycle, the heaters 50 and 52 are turned on full at least during a temperature sensing interval.

In this manner, the temperature in the sample vial is cycled according to the desired temperature profile. At the end of the run, the solenoid valve 72 is switched on and refrigerated air from the freezer chamber 74 is driven by fan 76 into the chamber 20.

Figure 7:
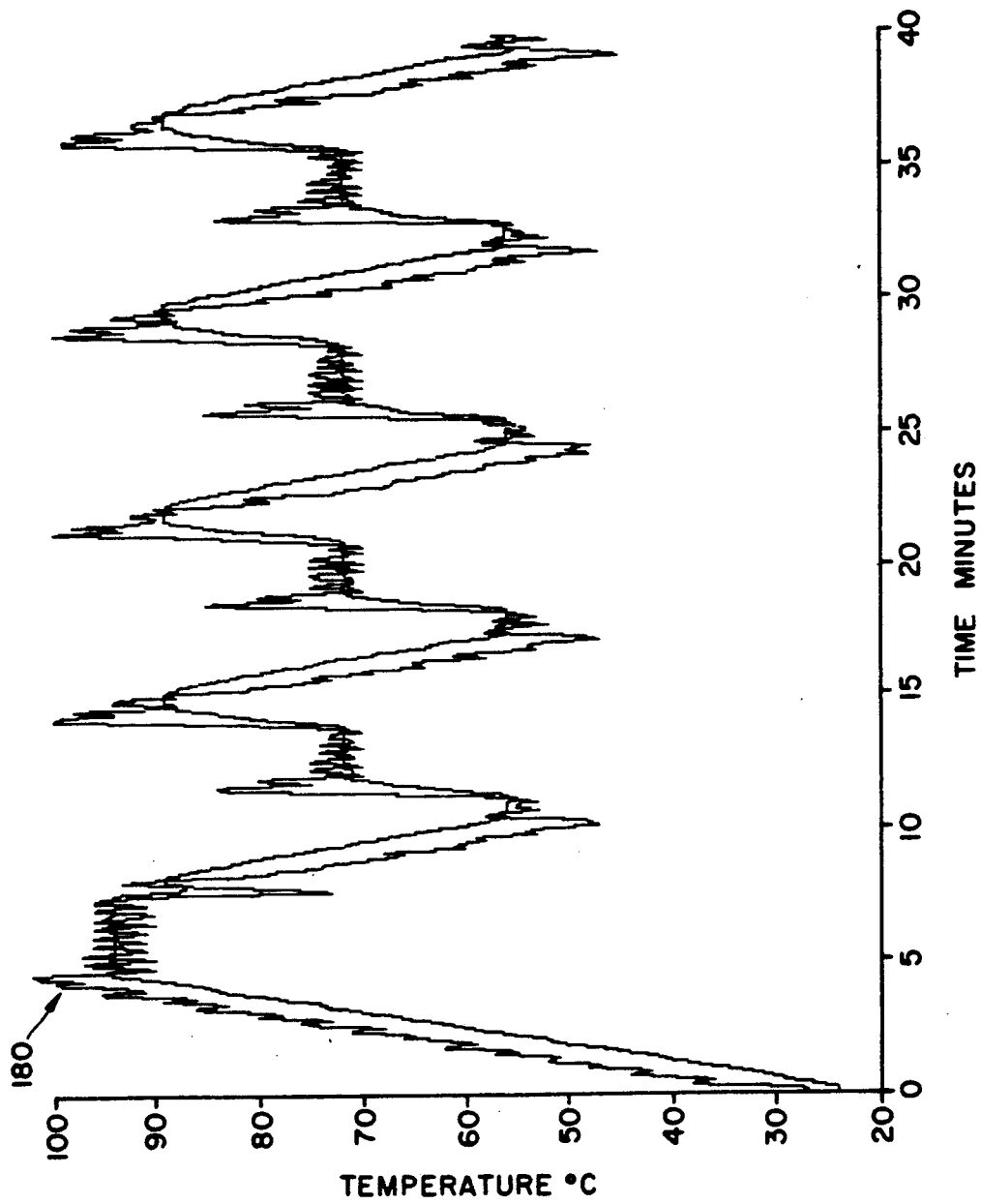
FIG. 7 is a graph showing sample vial temperature and chamber air temperature during operation of a thermal reactor according to the invention.

At the end of the run, the user may plot the desired temperature profile, and the actual temperature profiles of the temperatures as indicated by the vial sensor 90 and air sensor 92. For example, as shown in FIG. 7, the air temperature is shown as the rapidly varying line, and the vial temperature is shown as the steadier line. The oscillation of the air temperature, caused by rapid pulsing of the heaters 50 and 52, permits the temperature of the vial to be maintained at a level close to the desired temperature profile.

ALTERNATIVE EMBODIMENTS

While a preferred embodiment has been described, various configurations of components may be used. For example, it is possible, with some loss of Performance, to substitute a single air inlet for the two heated air hoses 30 and 32, and this single air inlet could be attached to a single turbine or by a Y connection to 2 turbines. The preferred configuration shown is used because it gives an even distribution of air throughout the chamber.

The square shape of the chamber is desirable because it creates turbulence for efficient mixing of the warm air entering the chamber. The turbulence creating fan 80 is desirable because it creates rapid mixing of the air, but other turbulence creating means could be used, with some possible loss of performance.

Cooling of the walls of the chamber 20, so that the walls of the chamber are kept at a relatively fixed temperature, and the use of air (which has a low thermal mass) for cooling the walls of the chamber, facilitates the precise control of the air temperature within the chamber, and consequently the temperature within the vials. Thus, while a water cooled block could be used for the chamber walls, it would have too high a thermal mass, and would reduce the controllability of the temperature profile and impede the response time.

The chamber also has use as a differential scanning calorimeter in which case the sample tray would be omitted, and substituted by a matched pair of chambers (sample and reference) placed inside the chamber 20.

It will therefore be understood that, while a preferred embodiment has been described, immaterial modifications of the invention could be made by persons skilled in the art, and these are intended to be covered by the scope of the claims which follow.

I claim:

1. A thermal reactor for cyclic heating and cooling of samples and being locatable in an environment having an ambient air supply, the thermal reactor comprising:

a chamber having means for securing the samples within the chamber;

air supply means connected to the chamber and to the ambient air outside the chamber, the air supply means including first and second air supply passageways connected to the chamber and first and second fans disposed in the first and second air supply passageways, respectively, for supplying air to the chamber;

an exhaust air passageway connecting the chamber and the ambient air outside the chamber for exhausting air from the chamber;

heating means disposed within at least one of the air supply passageways;

first temperature sensor means disposed within the chamber for sensing the temperature of a representative one of the samples, the first temperature sensor means having a first output representative of the temperature of the sample;

second temperature sensor means disposed within the chamber or the at least one of the air supply passageways for sensing the temperature of the air supplied to the chamber, the second temperature sensor means having a second output representative of the temperature of the air within the chamber; and control means connected to the first temperature sensor means, the second temperature sensor means and the heating means for cyclically controlling the temperature of the air supplied to the chamber by selectively and periodically heating the air in response to the first and second outputs so that the temperature of the sample follows a predetermined temperature profile.

2. The thermal reactor of claim 1 further comprising:
turbulence creating means disposed adjacent the air supply means and within the chamber for breaking up the laminar flow of air within at least one of the air supply passageways.

3. The thermal reactor of claim 2 in which the turbulence creating means comprises a fan having blades, the blades being disposed to interrupt the flow of air from at least one of the air supply passageways.

4. The thermal reactor of claim 1 in which the chamber is defined by internally porous walls, and the thermal reactor further including refrigeration means connected to the internally porous walls for providing cooled air to the walls.

5. The thermal reactor of claim 2 in which the chamber is defined by internally porous walls, and the thermal reactor further including refrigeration means connected to the internally porous walls for providing cooled air to the walls.

6. The thermal reactor of claim 1 in which the chamber is defined by veined walls and the thermal reactor further include refrigeration means connected to the veined walls for providing cooled air to the walls.

7. The thermal reactor of claim 2 in which the chamber is defined by veined walls and the thermal reactor further includes refrigeration means connected to the veined walls for providing cooled air to the walls.

8. The thermal reactor of claim 1 in which the fans in the air supply passageways operate continuously throughout a heating and cooling cycle.

9. The thermal reactor of claim 4 further including:
a cooling air passageway connected between the refrigeration means and the chamber;
means disposed on the cooling air passageway for opening and closing the cooling air passageway; and
the opening and closing means being controlled by the control means.

10. The thermal reactor of claim 5 further including:
a cooling air passageway connected between the refrigeration means and the chamber;
means disposed on the cooling air passageway for opening and closing the cooling air passageway; and
the opening and closing means being controlled by the control means.

11. A thermal reactor for cyclic heating and cooling of samples and being locatable in an environment having an ambient air supply, the thermal reactor comprising:

a chamber having means for securing the samples within the chamber, the chamber being defined by internally porous walls, and the thermal reactor further including refrigeration means connected to the internally porous walls for providing cooled air to the walls;

air supply means connected to the chamber and to the ambient air outside the chamber, the air supply means including an air supply passageway connected to the chamber and a fan disposed in the air supply passageway for supplying air to the chamber;

an exhaust air passageway connecting the chamber and the ambient air outside the chamber for exhausting air from the chamber;

heating means disposed within the air supply passageway;

first temperature sensor means disposed within the chamber for sensing the temperature of a representative one of the samples, the first temperature sensor means having a first output representative of the temperature of the sample;

second temperature sensor means disposed within the chamber or the air supply passageway for sensing the temperature of the air supplied to the chamber, the second temperature sensor means having a second output representative of the temperature of the air within the chamber; and control means connected to the first temperature sensor means, the second temperature sensor means and the heating means for cyclically controlling the temperature of the air supplied to the chamber by selectively and periodically heating the air in response to the first and second outputs so that the temperature of the sample follows a predetermined temperature profile.

12. A thermal reactor for cyclic heating and cooling of samples and being locatable in an environment having an ambient air supply, the thermal reactor comprising:

a chamber having means for securing the samples within the chamber, the chamber being defined by internally veined walls, and the thermal internally veined walls for providing cooled air to the walls;

air supply means connected to the chamber and to the ambient air outside the chamber, the air supply means including an air supply passageway connected to the chamber and a fan disposed in the air supply passageway for supplying air to the chamber;

an exhaust air passageway connecting the chamber and the ambient air outside the chamber for exhausting air from the chamber;

heating means disposed within the air supply passageway;

first temperature sensor means disposed within the chamber for sensing the temperature of a representative one of the samples, the first temperature sensor means having a first output representative of the temperature of the sample;

second temperature sensor means disposed within the chamber or the air supply passageway for sensing the temperature of the air supplied to the chamber, the second temperature sensor means having a second output representative of the temperature of the air within the chamber; and control means connected to the first temperature sensor means, the second temperature sensor means and the heating means for cyclically controlling the temperature of the air supplied to the chamber by selectively and periodically heating the air in response to the first and second outputs so that the temperature of the sample follows a predetermined temperature profile.

13. A method of cyclically heating and cooling samples in a chamber having a supply of ambient air, comprising:

providing a chamber having means for securing the samples within the chamber and means for receiving refrigerated air in the walls of the chamber;

supplying air to the chamber from the ambient air through air passage means;

sensing and producing a first signal corresponding to the temperature of a representative one of the samples;

sensing and producing a second signal corresponding to the temperature of the air in the chamber;

receiving the first and second signals at means; and cyclically controlling the temperature of the air supplied to the chamber by selectively and periodically supplying heated air to the chamber in response to the first and second signals so that the temperature of the representative one of samples follows a predetermined temperature profile.

14. The method of claim 13 in which the air passage means comprises warm air supply means connected to the chamber, the warm air supply means including an air supply passageway connected to the chamber and a fan disposed in the air supply passageway, a heater being disposed in the air supply passageway; and an exhaust air passageway connecting the chamber and the air outside the chamber, the method comprising:

controlling the temperature of the air supplied to the chamber by selectively operating the heater to heat the air supply to the chamber in response to receiving the first and second signals.

15. The method of claim 13 further comprising creating turbulence within the chamber.

16. The method of claim 13 in which the means for receiving refrigerated air comprises providing a chamber which has internally porous walls, and providing refrigerated air to the porous walls of the chamber.

17. The method of claim 13 in which the means for receiving refrigerated air comprises providing a chamber which has internally veined walls, and providing refrigerated air to the veined walls of the chamber.

18. The method of claim 14 further comprising continuously operating a fan in a air supply passageway to supply said ambient air to the chamber while selectively operating a heater to supply heated air to the chamber.

* * * * *

UNITED STATES PATENT AND TRADEMARK OFFICE
CERTIFICATE OF CORRECTION

PATENT NO. : 5,123,477

DATED : June 23, 1992

INVENTOR(S) : TYLER, Jonathan M.

It is certified that error appears in the above-identified patent and that said Letters Patent is hereby corrected as shown below:

On the title page: Item
"[73] Assignee: Unisys Corporation, Blue Bell, Pa." should be deleted.

Signed and Sealed this

Twenty-second Day of March, 1994

Attest:

BRUCE LEHMAN

Attesting Officer     Commissioner of Patents and Trademarks